Figure 1:
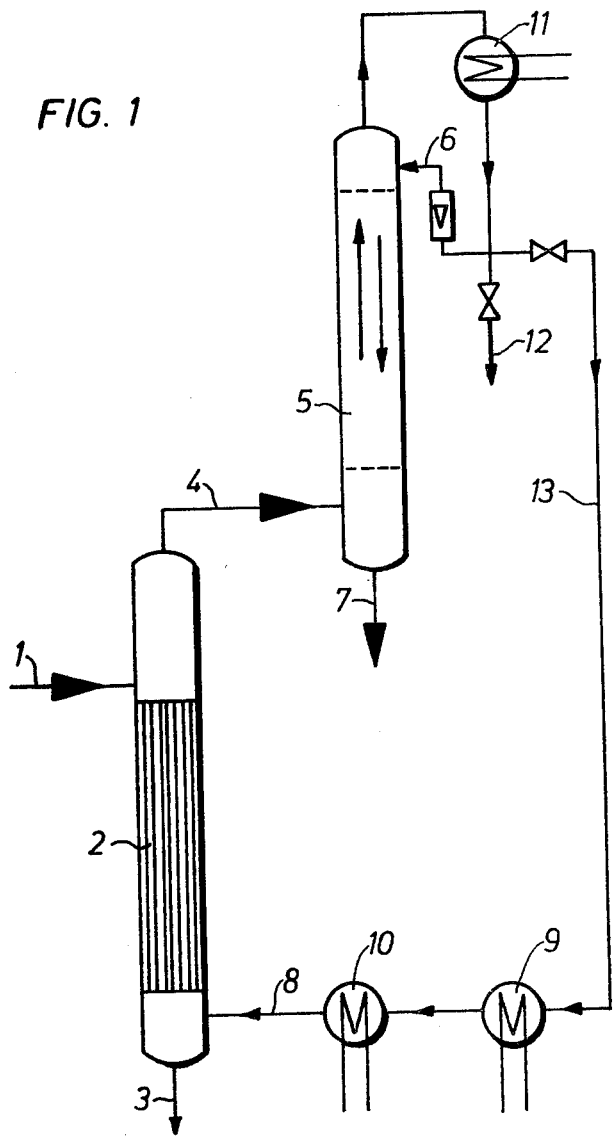

United States Patent [19]

Bauer et al.

[11] 4,090,922

[45] May 23, 1978

[54] CARRIER-VAPOR DISTILLATION

[75] Inventors: Kurt Bauer, Holzminden; Hans-Walter Brandt, Odenthal; Jürgen Schröter, Leverkusen, all of Germany

[73] Assignee: Bayer Aktiengesellschaft, Leverkusen, Germany

[21] Appl. No.: 765,034

[22] Filed: Feb. 2, 1977

Related U.S. Application Data

[63] Continuation of Ser. No. 682,878, May 3, 1976, abandoned, which is a continuation of Ser. No. 527,800, Nov. 27, 1974, abandoned.

[30] Foreign Application Priority Data

Dec. 12, 1973 Germany .............................. 2360977

[51] Int. Cl.² .................................................. B01D 9/02
[52] U.S. Cl. .......................................... 203/48; 203/49
[58] Field of Search .................... 203/49, 48, 50–52, 203/57; 23/307; 202/134, 185 A; 159/2 R

[56] References Cited

U.S. PATENT DOCUMENTS

| 3,378,467 | 4/1968 | Colton | 203/49 |
| 3,578,567 | 5/1971 | Malvin | 203/49 |
| 3,687,821 | 8/1972 | Zailes | 202/185 A |
| 3,694,322 | 9/1972 | Ikeda | 203/DIG. 3 |

Primary Examiner—Hiram H. Bernstein
Attorney, Agent, or Firm—Burgess, Dinklage & Sprung

[57] ABSTRACT

Process for the separation or purification of heat-sensitive compounds by carrier-vapor distillation, wherein the superheated solvent vapor which is loaded with the compound to be distilled is cooled by treatment with condensed solvent in counter-current and the amount of condensed solvent is measured in such a manner that a saturated solution of the compound which is almost at boiling point is formed from the superheated, loaded vapor. The process being especially apted for separating or purifying 4-hydroxybenzaldehydes optionally substituted by one or more $C_1$–$C_4$-alkoxy groups.

5 Claims, 1 Drawing Figure

U.S. Patent    May 23, 1978    4,090,922

CARRIER-VAPOR DISTILLATION

This is a continuation of application Ser. No. 682,878, filed May 3, 1976, now abandoned, which in turn is a continuation of application Ser. No. 527,800, filed Nov. 27, 1974, now abandoned.

The present invention relates to a new process for the separation or purification of heat-sensitive compounds by carrier-vapour distillation.

Carrier-vapour distillation is a known process for the purification of heat-sensitive compounds by distillation. It cannot, however, be employed for a number of compounds, as the thermal exposure even under the mild conditions of this distillation process is still too great, hence resulting in poor yields and/or unsatisfactory degrees of purity of the compounds.

A carrier-vapour distillation process has now been found in which the compounds to be distilled are subjected to such a low degree of thermal exposure that it can even be employed to distil extremely heat-sensitive compounds which are not distillable or are only distillable with decomposition by means of conventional carrier-vapour distillation processes. The process according to the invention consists in using the superheated vapour of an organic solvent as carrier-vapour and in cooling the superheated solvent vapour laden with the compound to be distilled by treating it with condensed solvent in counter-current and thereby measuring the quantity of condensed solvent in such a manner that a supersaturated solution of the compound with a temperature almost at boiling point is obtained from the laden, superheated vapour.

A solution at "about boiling temperature" is a solution which is at boiling temperature or a few degrees celsius lower, e.g., 1° to 3° C.

By subjecting the laden, superheated vapour to condensation by evaporation according to the invention, only one single process step is required to achieve (1) cooling of the vapour to the boiling temperature of the solvent employed, and
(2) concentration of the condensed vapour to a solution of the distilled compound which is saturated at the boiling point of the solvent.

By adopting the embodiment of the carrier-vapour distillation according to the invention, the compounds to be distilled are only subjected to higher temperatures for an extremely short period of time. This short period effects such an immense reduction of the thermal strain of the compounds to be distilled that decomposition no longer takes place. The compounds are obtained in an almost 100 % yield and are of high purity.

The carrier-vapour distillation according to the invention also has the technical advantage that the entire organic solvent employed in the process can be recovered in highly pure form and free of all traces of distilled compound and hence can be used again and again, that is, it can be recycled. A further technical advantage consists in that the purified compound is produced in the form of a homogeneous solution which can be easily separated off and out of which the compound crystallizes upon cooling.

The carrier-vapour used in the process according to the invention comes from organic solvents which are inert with respect to the product to be purified, which are able effectively to dissolve the compounds to be distilled, at least under heat, and out of which the distilled compounds crystallize and which are furthermore stable under high temperatures and easily condensable. Their boiling point under normal conditions should be in the range of about 60° to 190° C, preferably 100° to 150° C.

Basically, any organic compounds satisfying the requirements mentioned above are suitable for use as the organic solvents used as carrier-vapour. The following compounds are mentioned by way of example: aliphatic and alicyclic saturated hydrocarbons, such as, hexane, heptane, octane, nonane, decane, and cyclohexane and the derivatives of these compounds substituted by lower alkyl radicals; further benzene and benzene derivatives which may optionally be substituted by one or more lower alkyl radicals for example, toluene, ethylbenzene, n- and iso-propylbenzene, butylbenzene and trimethylbenzene; also halogenated (preferably chlorinated) derivatives of the aforementioned hydrocarbons for example, chlorobenzene or o-, m- and p-dichlorobenzenes. It is also possible to use aliphatic alcohols for example, ethanol, or chain-like or cyclic aliphatic ethers, for example, di-n-butyl ether, diisopropyl ether, and 1,4-dioxan; ketones for example, methylisobutyl ketone, and dipropyl ketone, as well as phenol and phenol ethers such as, anisol and phenetol.

It has proved particularly advantageous to use hexane, cyclohexane, benzene, toluene, ethylbenzene, chlorobenzene and anisol as carrier-vapour in the process according to the invention.

The distillation temperatures for the process according to the invention are in general between 110° and 220° C, preferably between 140° and 190° C.

The condensation by evaporation in accordance with the invention of the superheated, loaded vapour can be carried out under atmospheric pressure or subatmospheric of 100 mm Hg, e.g. 120, 150 or 360 mm Hg.

The process in accordance with the invention is preferably carried out in such a manner that the mixture or crude product 1 containing the compound to be distilled, or the solution of the mixture (crude product (1)), in the solvent employed as carrier-vapour is treated in a manner known per se in counter-current with superheated carrier-vapour in an evaporator 2. Any high boiling impurities, resins and inorganic compounds, which may be present in the mixture or crude product feed 1, will be immediately deposited in the sump 3 of the evaporator from where they can be drawn off. The superheated, loaded vapour 4, is thereafter conveyed into a column 5 where it is cooled and simultaneously concentrated by the onflowing condensed solvent 6 to form a solution 7 which is at approximately boiling temperature, but no longer actually boiling, and which is saturated with distilled compound.

The amount required of condensed solvent can be calculated from the temperature difference to be overcome: temperature of the superheated, loaded vapour — boiling temperature of the organic solvent used as carrier-vapour. It may also be empiracally determined, however, by adjusting the feed of condensed solvent 6 so that upon condensation by evaporation a solution 7 is produced which is at approximately boiling temperature, but no longer actually boiling, and which is saturated with distilled compound.

The same organic solvent is employed to produce carrier-vapour and to effect cooling.

The carrier-vapour distillation process according to the invention is suitable for the distillation of heat-sensitive, crystallizable, and at least vapour-distillable, organic compounds. As examples of such compounds there may be mentioned: oximes such as cyclohexanone-oxime; lactams such as, ε-caprolactam; aromatic nitro compounds such as, nitro-phenol ether e.g. nitro-anisol, nitro-diphenylamines and nitro-anilines e.g., 2,4-dinitro-aniline; halogenated anilines e.g., 2,4-dichloro-aniline; quinones such as, o- and p- benzoquinone; aromatic bis-hydroxy compounds such as, brenzcatechin and hydroquinone; substituted aromatic aldehydes such as, piperonal and anisaldehyde and phenols substituted by lower alkenyl radicals and lower alkoxy radicals such as, eugenol and isoeugenol.

It has proved particularly advantageous to employ the process according to the invention for the separation or purification by distillation of 4-hydroxy benzaldehydes optionally substituted by one or more $C_1$–$C_4$ alkoxy groups such as, 4-hydroxy benzaldehyde, 4-hydroxy-3-methoxy benzaldehyde (vanillin), 4-hydroxy-3-ethoxy benzaldehyde (ethyl vanillin), 4-hydroxy-3-propoxy benzaldehyde and 4-hydroxy-3-isopropoxy benzaldehyde.

With the aid of the process in accordance with the invention it is possible for the first time to distil these extremely heat-sensitive compounds without decomposition occurring, and in this way to effect separation e.g. from the reaction mixtures as are formed during the manufacutre of the compounds (cf. for example, Organic Reactions (1957), Vol. IX, page 37 et seq.; German OS 2.115.551).

EXAMPLE 1

The carrier-vapour distillation in accordance with the invention was carried out in the apparatus shown in FIG. 1. To produce the superheated carrier-vapour, 1,3 kg per hour of toluene were evaporated in the evaporator 9, and the toluene vapour obtained superheated in the second evaporator 10 to 160° C. The superheated toluene vapour 8 was laden in evaporator 2 (falling film evaporator) in counter-current with 3.3 kg per hour of a solution 1 of 2.6 % by weight of vanillin in toluene. The high-boiling components and inorganic compounds contained in feed 1, approximately 5 g per hour, were deposited in the sump 3 of the evaporator. The vapour 4 laden with vanillin was conveyed to the distillation column 5 (bubble-cap plate column) and condensed (partly condensed) there with condensed toluene 6, the reflux from condenser 11, in counter-current to such an extent that 135 g per hour of a saturated solution of vanillin in toluene at boiling point accumulated in the sump 7 of the column 5 out of which the vanillin crystallized upon cooling. The toluene free of vanillin which accumulated in the condenser 11 was divided into two currents after removal of the reflux 6 i.e. current 12, which was discharged and whose amount corresponded to the toluene content of the feed 1 (approximately 3.2 kg per hour) and current 13 (approximately 1.3 kg per hour) which was recycled to the evaporator 9.

By this method the vanillin was obtained in a practically 100 % yield in the form of white crystals.

EXAMPLE 2

Work was carried out as described in Example 1 except that ethyl vanillin (3-ethoxy-4-hydroxy benzaldehyde) was distilled instead of vanillin (3-methoxy-4-hydroxy benzaldehyde). 2.5 kg per hour of toluene carrier-vapour were laden with 4.5 kg per hour of a solution 1 of 3.3 % by weight of ethyl vanillin in toluene. Approximately 250 g per hour of a saturated solution 7 of ethyl vanillin in toluene at about boiling point was drawn off the sump of the column 5 out of which ethyl vanillin crystallized upon cooling in the form of colourless crystals. The ethyl vanillin was obtained in almost quantitative yield.

A product of the same purity was obtained in the same yield when ethyl benzene was used instead of toluene.

EXAMPLE 3

Work was carried out as in Example 1 except that 2.5 kg per hour of chlorobenzene were used as carrier-vapour instead of toluene. 2.5 g of a solution 1 of 10 % by weight vanillin in chlorobenzene were fed in 3.5 g per hour of high-boiling compounds accumulated in the sump of the evaporator 2. 400 g per hour of a saturated solution 7 of vanillin in chlorobenzene at about boiling point were drawn off the sump of the column out of which the vanillin crystallized upon cooling in the form of colourless crystals. Yield: almost quantitative.

A product of the same purity was obtained in the same yield when anisol was employed instead of chlorobenzene.

EXAMPLE 4

1.5 kg of anisol superheated to 180° C was loaded within 1.5 hours with the solution of 100 g of vanillin in 200 g of anisol.

Experiment (a)

The superheated, loaded vapour 4 was subjected to condensation by evaporation in column 5 as described in Example 1. Upon cooling 97 g of vanillin crystallized out of the hot, saturated solution 7 removed from the sump of the column in the form of colourless crystals.

Experiment (b)

The superheated, loaded vapour 4 was completely condensed in the conventional manner, and the dilute solution of vanillin in anisol thereafter concentrated in vacuo ( < 5 mm Hg) until a saturated solution of aldehyde had formed. On cooling the concentrated solution, 79 g of vanillin crystallized out in the form of reddish-brown crystals: in addition 20 g of a resin-like residue was obtained.

What we claim is:

1. In the separation of a heat-sensitive compound by carrier-vapor distillation with the vapor of an organic solvent for the compound, the improvement which comprises passing superheated solvent vapor through a solution of the compound in the solvent to form a gaseous mixture of the solvent and the compound counter currently, contacting said gaseous mixture with previously condensed solvent to provide a liquid bottom product and to distill off a gaseous solvent vapor top product, the proportions of gaseous mixture and condensed solvent being such that the liquid bottom product is a saturated solution of the compound in the solvent almost at the boiling point of the formed solution, cooling said solution thereby to effect crystallization of the compound, withdrawing the gaseous solvent vapor top product and cooling it to form said previously condensed solvent, and separating the crystallized compound from said solution.

2. The process as claimed in claim 1, wherein the solvent is a member selected from the group consisting of hexane, cyclohexane, benzene, toluene, ethyl benzene and anisol.

3. The process as claimed in claim 1, wherein said counter current contact is effected at a temperature of 110° to 220° C.

4. The process as claimed in claim 1, where the compound is selected from the group consisting of 4-hydroxy benzaldehydes and 4-hydroxy benzaldehydes substituted by at least one $C_1$–$C_4$ alkoxy group.

5. The process as claimed in claim 1, wherein the compound is vanillin.

* * * * *